United States Patent
Spriggs et al.

(10) Patent No.: US 6,613,320 B1
(45) Date of Patent: Sep. 2, 2003

(54) DEFECTIVE CD4+T-CELLS THAT EXPRESS ACTIVE CD40-L

(75) Inventors: Melanie K. Spriggs, Seattle, WA (US); Richard J. Armitage, Bainbridge Island, WA (US); William C. Fanslow, III, Federal Way, WA (US); Michael B. Widmer, Seattle, WA (US); Barry L. Davison, Mercer Island, WA (US); Blair R. Renshaw, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/545,993

(22) Filed: Apr. 10, 2000

Related U.S. Application Data

(63) Continuation of application No. 08/589,771, filed on Jan. 22, 1996, now Pat. No. 6,106,832, which is a division of application No. 08/184,422, filed on Jan. 21, 1994, now Pat. No. 5,565,321, which is a continuation-in-part of application No. 08/009,258, filed on Jan. 22, 1993, now abandoned.

(51) Int. Cl.$^7$ ................................................ C12N 5/10

(52) U.S. Cl. .................. 424/93.21; 424/93.1; 424/93.2; 424/93.7; 424/93.71; 434/455

(58) Field of Search ............................. 424/93.7, 93.71; 435/455

(56) References Cited

U.S. PATENT DOCUMENTS 6,087,329 A * 7/2000 Armitage et al.

OTHER PUBLICATIONS

Skolnick et al. Trends in Biotechnology 18:34–39 (2000).*
Aruffo et al. Cell 72: 291–300 (1993).*
Graf et al. Eur. J. Immunol 22: 3191–3194 (1992).*
Padayachee et al. Genomics 14: 551–553 (1992).*
Mayer et al. N. Eng. J. Med. 314: 409–413 (1986).*

* cited by examiner

Primary Examiner—Phillip Gambel
(74) Attorney, Agent, or Firm—Janis C. Henry

(57) ABSTRACT

CD4+ cells obtained from individuals with defective CD40L gene and transfected with a vector containing CD40-L are described.

1 Claim, 4 Drawing Sheets

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO: 1:

CCAGAAGATA CCATTTC                                       17

(2) INFORMATION FOR SEQ ID NO: 2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO: 2:

AGCCCACTGT AACACAG                                       17

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 3:

CATGTCATAA GTGAGGC                                        17

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 4:

CATAAGGAGG ATCCTAG                                        17

(2) INFORMATION FOR SEQ ID NO: 5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 5:

TGCGGGCAAC AATCCATTCA CTTGGGAGTA GTATTTGAAT TGCAA            45

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 6:

CCATGAGCAA CAACTTGGTA ACCCCGGAAA ATGGGAAACA GC              42

(2) INFORMATION FOR SEQ ID NO: 7:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:

(B) CLONE: CD40-L (ix) FEATURE:
 (A) NAME/KEY: CDS
 (B) LOCATION: 46..831

(xi) SEQUENCE DESCRIPTION: SEQ ID NO: 7:

| | | | |
|---|---|---|---|
| TGCCACCTTC TCTGCCAGAA GATACCATTT CAACTTTAAC ACAGC ATG ATC GAA | | | 54 |
| Met Ile Glu | | | |
| 1 | | | |

| | | | | | | | | | | | | | | | |
|---|---|---|---|---|---|---|---|---|---|---|---|---|---|---|---|
| ACA | TAC | AAC | CAA | ACT | TCT | CCC | CGA | TCT | GCG | GCC | ACT | GGA | CTG | CCC | ATC | 102 |
| Thr | Tyr | Asn | Gln | Thr | Ser | Pro | Arg | Ser | Ala | Ala | Thr | Gly | Leu | Pro | Ile | |
| | 5 | | | | 10 | | | | | 15 | | | | | | |

| | | | | | | | | | | | | | | | |
|---|---|---|---|---|---|---|---|---|---|---|---|---|---|---|---|
| AGC | ATG | AAA | ATT | TTT | ATG | TAT | TTA | CTT | ACT | GTT | TTT | CTT | ATC | ACC | CAG | 150 |
| Ser | Met | Lys | Ile | Phe | Met | Tyr | Leu | Leu | Thr | Val | Phe | Leu | Ile | Thr | Gln | |
| 20 | | | | | 25 | | | | | 30 | | | | | 35 | |

| | | | | | | | | | | | | | | | |
|---|---|---|---|---|---|---|---|---|---|---|---|---|---|---|---|
| ATG | ATT | GGG | TCA | GCA | CTT | TTT | GCT | GTG | TAT | CTT | CAT | AGA | AGG | TTG | GAC | 198 |
| Met | Ile | Gly | Ser | Ala | Leu | Phe | Ala | Val | Tyr | Leu | His | Arg | Arg | Leu | Asp | |
| | | | | 40 | | | | | 45 | | | | | 50 | | |

| | | | | | | | | | | | | | | | |
|---|---|---|---|---|---|---|---|---|---|---|---|---|---|---|---|
| AAG | ATA | GAA | GAT | GAA | AGG | AAT | CTT | CAT | GAA | GAT | TTT | GTA | TTC | ATG | AAA | 246 |
| Lys | Ile | Glu | Asp | Glu | Arg | Asn | Leu | His | Glu | Asp | Phe | Val | Phe | Met | Lys | |
| | | | | 55 | | | | | 60 | | | | | 65 | | |

| | | | | | | | | | | | | | | | |
|---|---|---|---|---|---|---|---|---|---|---|---|---|---|---|---|
| ACG | ATA | CAG | AGA | TGC | AAC | ACA | GGA | GAA | AGA | TCC | TTA | TCC | TTA | CTG | AAC | 294 |
| Thr | Ile | Gln | Arg | Cys | Asn | Thr | Gly | Glu | Arg | Ser | Leu | Ser | Leu | Leu | Asn | |
| | | 70 | | | | | 75 | | | | | 80 | | | | |

| | | | | | | | | | | | | | | | |
|---|---|---|---|---|---|---|---|---|---|---|---|---|---|---|---|
| TGT | GAG | GAG | ATT | AAA | AGC | CAG | TTT | GAA | GGC | TTT | GTG | AAG | GAT | ATA | ATG | 342 |
| Cys | Glu | Glu | Ile | Lys | Ser | Gln | Phe | Glu | Gly | Phe | Val | Lys | Asp | Ile | Met | |
| 85 | | | | | 90 | | | | | 95 | | | | | | |

| | | | | | | | | | | | | | | | |
|---|---|---|---|---|---|---|---|---|---|---|---|---|---|---|---|
| TTA | AAC | AAA | GAG | GAG | ACG | AAG | AAA | GAA | AAC | AGC | TTT | GAA | ATG | CAA | AAA | 390 |
| Leu | Asn | Lys | Glu | Glu | Thr | Lys | Lys | Glu | Asn | Ser | Phe | Glu | Met | Gln | Lys | |
| 100 | | | | | 105 | | | | | 110 | | | | | 115 | |

| | | | | | | | | | | | | | | | |
|---|---|---|---|---|---|---|---|---|---|---|---|---|---|---|---|
| GGT | GAT | CAG | AAT | CCT | CAA | ATT | GCG | GCA | CAT | GTC | ATA | AGT | GAG | GCC | AGC | 438 |
| Gly | Asp | Gln | Asn | Pro | Gln | Ile | Ala | Ala | His | Val | Ile | Ser | Glu | Ala | Ser | |
| | | | | 120 | | | | | 125 | | | | | 130 | | |

| | | | | | | | | | | | | | | | |
|---|---|---|---|---|---|---|---|---|---|---|---|---|---|---|---|
| AGT | AAA | ACA | ACA | TCT | GTG | TTA | CAG | TGG | GCT | GAA | AAA | GGA | TAC | TAC | ACC | 486 |
| Ser | Lys | Thr | Thr | Ser | Val | Leu | Gln | Trp | Ala | Glu | Lys | Gly | Tyr | Tyr | Thr | |
| | | | 135 | | | | | 140 | | | | | 145 | | | |

| | | | | | | | | | | | | | | | |
|---|---|---|---|---|---|---|---|---|---|---|---|---|---|---|---|
| ATG | AGC | AAC | AAC | TTG | GTA | ACC | CTG | GAA | AAT | GGG | AAA | CAG | CTG | ACC | GTT | 534 |
| Met | Ser | Asn | Asn | Leu | Val | Thr | Leu | Glu | Asn | Gly | Lys | Gln | Leu | Thr | Val | |
| | | 150 | | | | | 155 | | | | | 160 | | | | |

| | | | | | | | | | | | | | | | |
|---|---|---|---|---|---|---|---|---|---|---|---|---|---|---|---|
| AAA | AGA | CAA | GGA | CTC | TAT | TAT | ATC | TAT | GCC | CAA | GTC | ACC | TTC | TGT | TCC | 582 |
| Lys | Arg | Gln | Gly | Leu | Tyr | Tyr | Ile | Tyr | Ala | Gln | Val | Thr | Phe | Cys | Ser | |
| 165 | | | | | 170 | | | | | 175 | | | | | | |

| | | | | | | | | | | | | | | | |
|---|---|---|---|---|---|---|---|---|---|---|---|---|---|---|---|
| AAT | CGG | GAA | GCT | TCG | AGT | CAA | GCT | CCA | TTT | ATA | GCC | AGC | CTC | TGC | CTA | 630 |
| Asn | Arg | Glu | Ala | Ser | Ser | Gln | Ala | Pro | Phe | Ile | Ala | Ser | Leu | Cys | Leu | |
| 180 | | | | | 185 | | | | | 190 | | | | | 195 | |

| | | | | | | | | | | | | | | | |
|---|---|---|---|---|---|---|---|---|---|---|---|---|---|---|---|
| AAG | TCC | CCC | GGT | AGA | TTC | GAG | AGA | ATC | TTA | CTC | AGA | GCT | GCA | AAT | ACC | 678 |
| Lys | Ser | Pro | Gly | Arg | Phe | Glu | Arg | Ile | Leu | Leu | Arg | Ala | Ala | Asn | Thr | |
| | | | | 200 | | | | | 205 | | | | | 210 | | |

| | | | | | | | | | | | | | | | |
|---|---|---|---|---|---|---|---|---|---|---|---|---|---|---|---|
| CAC | AGT | TCC | GCC | AAA | CCT | TGC | GGG | CAA | CAA | TCC | ATT | CAC | TTG | GGA | GGA | 726 |
| His | Ser | Ser | Ala | Lys | Pro | Cys | Gly | Gln | Gln | Ser | Ile | His | Leu | Gly | Gly | |
| | | | 215 | | | | | 220 | | | | | 225 | | | |

| | | | | | | | | | | | | | | | |
|---|---|---|---|---|---|---|---|---|---|---|---|---|---|---|---|
| GTA | TTT | GAA | TTG | CAA | CCA | GGT | GCT | TCG | GTG | TTT | GTC | AAT | GTG | ACT | GAT | 774 |
| Val | Phe | Glu | Leu | Gln | Pro | Gly | Ala | Ser | Val | Phe | Val | Asn | Val | Thr | Asp | |
| | | 230 | | | | | 235 | | | | | 240 | | | | |

| | | | | | | | | | | | | | | | |
|---|---|---|---|---|---|---|---|---|---|---|---|---|---|---|---|
| CCA | AGC | CAA | GTG | AGC | CAT | GGC | ACT | GGC | TTC | ACG | TCC | TTT | GGC | TTA | CTC | 822 |
| Pro | Ser | Gln | Val | Ser | His | Gly | Thr | Gly | Phe | Thr | Ser | Phe | Gly | Leu | Leu | |
| 245 | | | | | 250 | | | | | 255 | | | | | | |

| | | |
|---|---|---|
| AAA CTC TGAACAGTGT CA | | 840 |
| Lys Leu | | |
| 260 | | |

(2) INFORMATION FOR SEQ ID NO: 8:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ile Glu Thr Tyr Asn Gln Thr Ser Pro Arg Ser Ala Ala Thr Gly
 1               5                  10                  15

Leu Pro Ile Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
             35                  40                  45

Arg Leu Asp Lys Ile Glu Asp Glu Arg Asn Leu His Glu Asp Phe Val
         50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

(2) INFORMATION FOR SEQ ID NO: 9:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 9:

GGCAAGGTCA AGCTCATCC        19

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 10:

```
GATATTGCTG AAGAGCTTGG                                              20
```

(2) INFORMATION FOR SEQ ID NO: 11:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 11:

```
GTATGTGGCT GAACACCTG                                               19
```

(2) INFORMATION FOR SEQ ID NO: 12:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 12:

```
CTTGTGTAGC GCCAAGTG                                                18
```

(2) INFORMATION FOR SEQ ID NO: 13:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 13:

```
CCCAAGTGTA TGAGCATGTG TGT                                          23
```

(2) INFORMATION FOR SEQ ID NO: 14:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 14:

```
GTTCCTCCAC CTAGTCATTC ATC                                          23
```

(2) INFORMATION FOR SEQ ID NO: 15:

(i) SEQUENCE CHARACTERISTICS:

```
        (A) LENGTH: 22
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 15:

GCCCTGAATG AACTGCAGGA CG                                              22

(2) INFORMATION FOR SEQ ID NO: 16:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 16:

CACGGGTAGC CAACGCTATG TC                                              22
```

DEFECTIVE CD4+T-CELLS THAT EXPRESS ACTIVE CD40-L

CROSS-REFERENCE TO RELATED APPLICATION

This application is a continuation of application 08/589,771 file Jan. 22, 1996, now U.S Pat. No. 6,106,832, which is a divisional application 08/184,422 filed Jan. 21, 1994, now U.S. Pat. No. 5,565,321, which is a continuation-in-part of application Ser. No. 08/009,258 filed Jan. 22, 1993, now abandoned.

TECHNICAL FIELD OF THE INVENTION

The present invention relates to a ligand for the cell-surface antigen CD40, CD40 ligand (CD40L). More specifically, the present invention relates to methods of detecting mutations in a CD40L gene, and to methods of treating a syndrome that results in elevated levels of serum IgM and diminished levels of all other isotypes of immunoglobulins.

BACKGROUND OF THE INVENTION

Human X-linked hyper-IgM syndrome is characterized by an elevated level of serum IgM and diminished (virtually undetectable) levels of other isotypes of immunoglobulins. Affected males usually experience onset of recurrent infection in the first year of life. The clinical course may include intermittent neutropenia and Pneumocystis pneumonia, as well as infections that are more typical of hypogammaglobulinemia, such as bacterial otitis, sinusitis, and pneumonia. This condition is lethal in the absence of medical intervention; however, patients typically respond well to a maintenance therapy consisting of intravenous gamma globulin, especially if therapy is initiated soon after birth.

Affected males have normal numbers of circulating B and T lymphocytes, although lymph node hyperplasia with an absence of germinal centers is common (Notarangelo et al., *Annu. Rev. Immunol.* 10:215, 1992). B-cells from such patients appear to be normal in that they can be induced to undergo isotype switching when cultured in vitro with a T cell line known to induce class switching in normal B-cell cultures (Hendricks et al., *Eiur. J. Immunol.* 20:2603, 1990; Mayer et al., *N. Engl. J. Med.* 314:409, 1986).

Elevated levels of serum IgM occur in other syndromes, including combined variable immune deficiency (CVID) and post congenital rubella. Alterations of T-cell activation either as a result of primary genetic immune deficiency or acquired CD4+ T-cell abnormality (e.g. AIDS) may also cause loss of CD40L-induced B-cell activation signals and thus partially explain the secondary abnormalities of B-cell function observed in these conditions.

The CD40 cell surface antigen has been shown to play an important role in B-cell proliferation and differentiation. Human CD40 protein (CD40), a cell-surface antigen present on the surface of B cells, is a peptide of 277 amino acids having a molecular weight of 30,600, with a 19 amino acid secretory signal peptide comprising predominantly hydrophobic amino acids. A cDNA encoding human CD40 was isolated from a cDNA library prepared from Burkitt lymphoma cell line Raji (Stamenkovic et al., *EMBO J.* 8:1403, 1989).

Activated CD4+ T cells express high levels of a ligand for CD40 (CD40L). Human CD40L, a membrane-bound glycoprotein, has recently been cloned from peripheral blood T-cells as described in Spriggs et al., *J.Exp. Med.* 176:1543 (1992), and in U.S. patent application Ser. No. 07/969,703, filed Oct. 23, 1992, the disclosure of which is incorporated by reference herein. The cloning of murine CD40L is described in Armitage et al., *Nature* 357:80, 1992. CD40L induces B-cell proliferation and secretion of various immunoglobulin isotypes (except IgE) in the absence of any co-stimulus, and can also induce production of IgE in the presence of cytokines.

CD40L thus appears to play a critical role in the cognate interaction between CD4+ T helper cells and B cells. A more detailed analysis of patients with X-linked hyper IgM syndrome and its related syndromes will provide valuable information on the T cell-B cell interactions involved in the humoral immune response. Early detection of X-linked hyper IgM syndrome and its related syndromes will allow prompt initiation of appropriate therapy.

Therefore, there is a need in the art to develop methods of detecting and confirming X-linked hyper IgM syndrome and other abnormalities in B cell-T cell interactions in which CD40 and CD40L play a role. Alternative methods of treatment of such syndromes are also needed.

SUMMARY OF THE INVENTION

The present invention relates to methods of detecting a mutation or mutations in a CD40L gene, comprising isolating nucleic acid (RNA or DNA) from an individual, selectively amplifying nucleic acid derived from the CD40 ligand gene and analyzing the amplified nucleic acid to determine if there is a mutation (or mutations) in the CD40L gene. Mutations in this gene result in abnormalities in the interaction of CD40L and CD40, which result in alterations in the interactions of T cells and B cells. Such alterations in T cell-B cell interaction play a role in X-linked hyper-IgM syndrome in a human, and may also occur in other syndromes.

The present invention further provides a method of treating an individual that has a syndrome in which the interaction of T cells and B cells is affected (such as X-linked hyper-IgM syndrome), comprising administering an effective amount of a soluble CD40L. Soluble forms of CD40L comprise the extracellular region of CD40L, and include, for example, fusion proteins comprising the extracellular region of CD40L and an Fc region of a human immunoglobulin, and CD40L multimers formed by adding a multimer-forming peptide to the extracellular region of CD40L.

The present invention also provides a method of utilizing gene therapy to correct X-linked hyper-IgM syndrome and other syndromes in which the CD40L gene does not encode biologically active CD40L. Gene therapy to correct such syndromes comprises isolating CD4+ T cells from an affected individual, transfecting the isolated T cells with a transfection vector that expresses a biologically active CD40L, and administering the transfected T cells expressing biologically active CD40L to the individual.

Also provided are animals that, through gene targeting technology utilizing embryonic stem cells, express non-functional CD40-L in vivo. Such animals, which are referred to as knockout animals, provide an non-human model useful is studying the cognate interaction of T and B cells in vivo.

DETAILED DESCRIPTION OF THE INVENTION

Figure 1A:
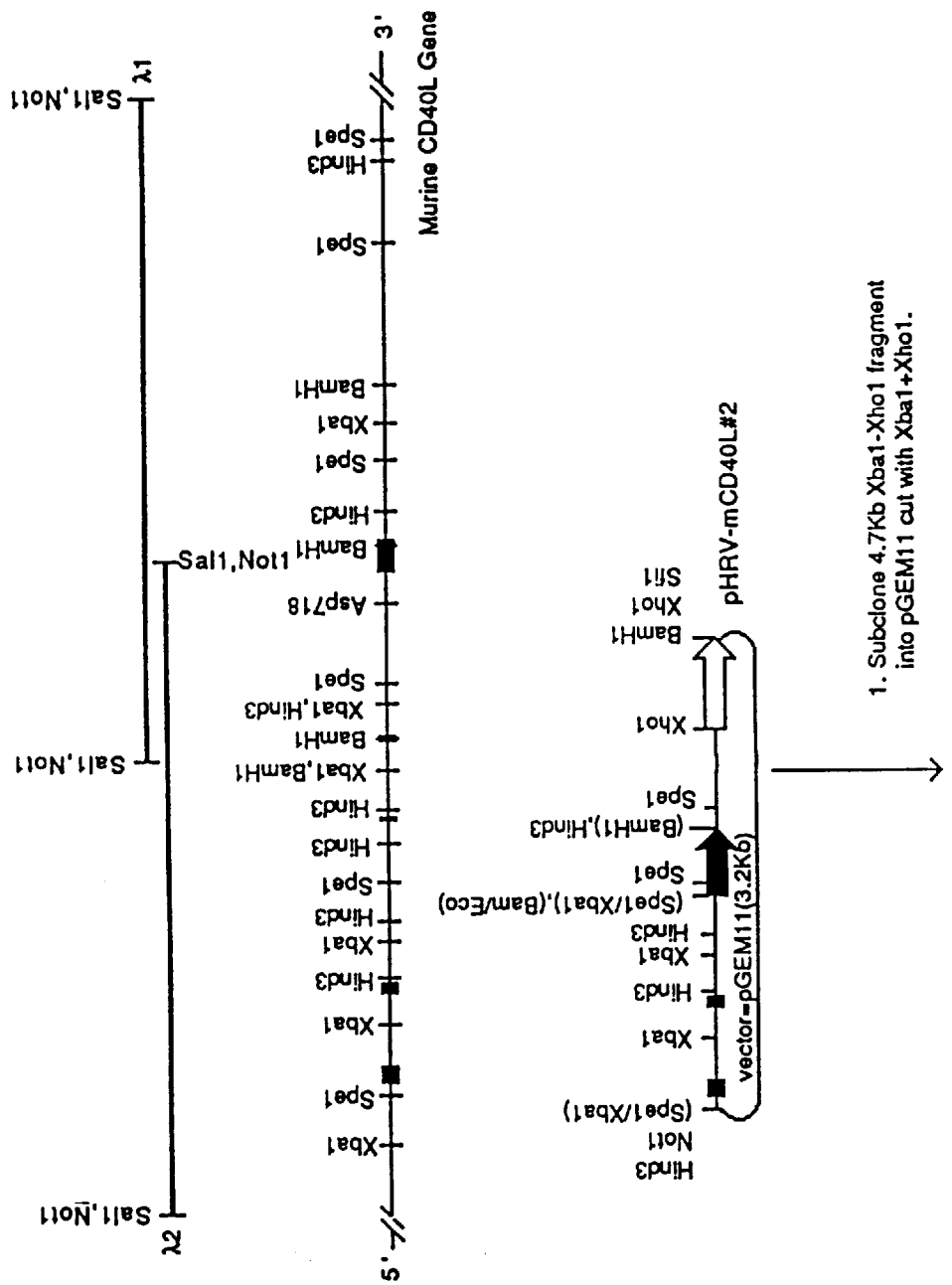
FIG. 1 is a flow chart representing construction of a targetting vector used to generate CD40-L knockout mice. Exons are represented on the map of the CD40-L gene as solid black boxes, and are numbered 1 through 5 from left to right. The solid black arrows represent the PGK-Neo gene; the large open arrows represent the HSV TK gene.

The present invention relates to syndromes or conditions in which the interaction between T cells and B cells is abnormal due to a defect in a gene encoding a membrane bound ligand for CD40. CD40, a member of the TNF receptor super family, is a membrane-bound receptor protein found to be expressed on B lymphocytes, epithelial cells and some carcinoma cell lines. Monoclonal antibodies directed against CD40 mediate various functional effects of human B cells, including homotypic adhesions, increased cell size, proliferation of B cells activated with anti-IgM, anti-CD20 monoclonal antibody (mAb), phorbol ester alone or phorbol ester combined with interleukin-4 (IL-4), and production of IgE and IgM from IL-4 stimulated, T cell-depleted cultures. These results suggest the importance of CD40 and CD40L in the proliferation and differentiation of B cells.

CD40L is a membrane-bound polypeptide with an extracellular region at its C terminus, a transmembrane region, and an intracellular region at its N-terminus. A soluble version of CD40L can be made from the extracellular region or a fragment thereof. The biological activity of CD40L is mediated by binding to CD40, and comprises proliferation of B cells and induction of immunoglobulin secretion from activated B cells. CD40L (including soluble oligomeric forms, as well as membrane-bound forms) can effect B cell proliferation and immunoglobulin secretion (except IgE secretion) without the presence of added IL-4, in contrast to anti-CD40 antibodies, which require IL4 and cross-linking to mediate activity. The cloning of CD40L and certain of its various activities are described in U.S. patent application Ser. No. 07/969,703, filed Oct. 23, 1992.

The gene for CD40L has been mapped to the proximal region of the murine X chromosome, linked to the Hprt locus. In situ hybridization studies of human metaphase chromosomes using a human CD40L cDNA probed confirmed a similar location in humans, with the largest number of grains mapping to band q26. The in vitro biological data on the function of the CD40L together with its chromosomal location suggested that this gene may play a role in an X-linked immunodeficiency. In particular, the phenotype of patients with X-linked hyper-IgM syndrome, and the linkage map position of this syndrome, were most consistent with a defect in the expression of a functional CD40L. X-linked hyper IgM syndrome has been mapped to Xq26, near HPRT (Padayachee et al., *Genomics* 14:551, 1992; Mensink et al., *Hum. Genet.* 76:96, 1987).

Expression of the CD40L gene was examined in patients with primary X-linked hyper-IgM syndrome, using peripheral blood T cells purified by separation over ficoll-hypaque, then activated with immobilized monoclonal antibody to CD3. Soluble CD40 protein (a fusion protein containing the extracellular domain of human CD40 fused to the Fc region of human IgG1; referred to herein as CD40.Fc, described in U.S. Ser. No. 07/969,703 and in Fanslow et al., *J. Immunol.* 149:655, 1992) was used to analyze the stimulated T cells by fluorescence activated cell sorting (FACS). Control cells (purified T cells from normal adult donors and/or a patient diagnosed with an unrelated X-linked immune deficiency) were analyzed in the same manner. T cells from the X-linked hyper IgM patients failed to express any detectable CD40L upon activation by CD3 antibody (although in some experiments, activated T cells from one patient appeared to weakly bind CD40), but did express the alpha chain of the IL-2 receptor (a T-cell surface activation marker), at levels comparable to that seen on T cells from control donors. T cells from hyper-IgM patients also showed normal proliferative responses to PHA or CD3 mAb plus IL-7.

RNA was extracted from patient and donor cells stimulated as described, and used to generate cDNA which served as a template for PCR reactions. Nucleotide sequence analysis of the resultant cDNAs indicated that single point mutations occurred in the CD40L of three of the four hyper-IgM patients. Each nucleotide change was unique, and all occurred in the extracellular domain of the CD40L. The CD40L cDNA generated from a fourth patient did not appear to contain any nucleotide changes within the coding region, indicating that another mechanism, possibly involving the 5' or 3' non-coding sequences, must be responsible for the absence of the CD40L on T cells from this patient To ensure that these mutations were not merely naturally occurring gene polymorphisms, two of the nucleotide changes found were introduced separately into a mammalian expression vector containing the complete coding region for the human CD40L using site-directed mutagenesis. Cells were transfected with vectors carrying either the wild type or the mutagenized CD40Ls, metabolically radiolabeled, and examined for expression of CD40L protein by precipitation with a polyclonal serum directed against CV1/EBNA cells expressing the human CD40L, or with CD40.Fc. Cells transfected with the wild type CD40L expressed a 33 kD protein that was detected using CD40.Fc. In contrast, cells transfected with either mutant form of CD40L did not express a protein recognized by CD40.Fc. Immunoprecipitation of identical lysates using the polyclonal antiserum resulted in the recognition of a 33 kD protein, from both mutant and wild type transfected cells, which co-migrated with the CD40L protein recognized by CD40.Fc. Northern blot analysis showed similar levels of CD40L-specific RNA in both wild type and mutant transfected cells. Additionally, cells transfected with either mutant form of CD40L were completely negative for CD40.Fc binding, while cells expressing the wild type CD40L showed strong CD40.Fc binding. Cells expressing either form of mutagenized CD40L were also unable to induce B cell proliferation or IgE secretion, confirming the absence of functional CD40L on their cell surfaces.

T cell-depleted peripheral blood mononuclear cells (PBMC; B-cell enriched populations) from X-linked hyper IgM patients showed a proliferative response to CD40L comparable to that seen with similarly purified PBMC from control donors. PBMC from normal donors produced measurable amounts of IgE when cultured with IL-4, whereas no IgE production was detected in cells from any of the hyper-IgM patients cultured under the same conditions. The addition of recombinant CD40L or a CD40 mAb to cultures containing hyper-IgM patients' PBMC restored the the ability of PBMC from three of four patients to secrete IgE.

The results of these studies illustrate the critical role CD40L appears to play in the cognate interaction between CD4+ T helper cells and B cells. This interaction is one of the principal requirements of a successful humoral immune response to most antigens. Further study of hyper-IgM syndrome and related syndromes will provide valuable information on the structural/functional relationship of CD40 and CD40L, and on interactions of the different cells involved in the humoral immune response. Methods of detecting abnormalities in CD40L will provide clarification of the various putative forms (autosomal recessive, autosomal dominant) of hyper-IgM syndrome, as well as other abnormalities in B cell-T cell interactions in which CD40 and CD40L play a role.

Mutations in CD40L can be detected by isolating nucleic acid (DNA or RNA) from an individual, selectively amplifying nucleic acid derived from a CD40L gene, and analyzing the amplified nucleic acid to determine if there is a mutation or mutations in the CD40L gene. Nucleic acids can be isolated from cells such as peripheral blood cells, or fetal cells obtained through amniocentesis or chorionic villus sampling. Other sources of nucleic acids included biopsy tissues, and other tissue samples in which nucleic acids are present.

Nucleic acids may be amplified through polymerase chain reaction (PCR), which utilizes oligonucleotide probes specific for a CD40L gene to selectively hybridize to and amplify those nucleic acids that are derived from the CD40L gene. Oligonucleotide probes that are useful in amplifying RNA derived from the CD40L gene include those probes defined by SEQ ID NOs:1 through 4. Additional oligonucleotide probes derived from the sequence of CD40L gene may be used to analyze the 5' and 3' noncoding regions of the nucleic acid, as well as the sequence of any introns present in the CD40L gene which are not transcribed into mRNA but may affect expression of a functional CD40L gene product.

Nucleic acid may be analyzed to determine if there is a mutation or mutations in a gene by performing nucleotide sequence analysis. Nucleotide sequence analysis may be performed manually, for example by a dideoxy analog chain termination technique. Alternatively, an automated sequencer may be used to perform nucleotide sequence analysis. The nucleotide sequence of the amplified nucleic acid is compared to the published sequence of CD40L (SEQ ID NO:7), which is also disclosed in U.S. Ser. No. 07/969, 703, the disclosure of which has been incorporated by reference, and Spriggs et al., *J.Exp. Med.* 176:1543 (1992).

Differences in the nucleotide sequence between the amplified nucleic acid and the published sequence of CD40L may result in mutations in a CD40L peptide expressed from the nucleic acid. Such mutations include substitution of a different amino acid (or amino acids) in the CD40L peptide, deletion of one or more amino acids from the CD40L peptide, premature termination of the CD40L peptide, and addition of amino acids to the CD40L peptide. Other types of mutations may cause improper splicing of exons, frame shifts that result in unreadable (nonsense) nucleic acid codons, or affect other elements required for transcription and translation of a biologically active CD40L. Mutations may thus be either in the coding region of a CD40L gene, or in the non-coding regions of the CD40L gene.

The effect of a mutation or mutations on the expression of a biologically active CD40L may be evaluated by introducing the mutation or mutations into an expression vector that encodes biologically active CD40L. A cloning vector containing human CD40L sequence, designated hCD40-L, was deposited with the American Type Culture Collection, Rockville, Md. (ATCC) on Dec. 6, 1991, under accession number 68873. Mutants can be constructed, for example, by using the gene splicing by overlap extension (SOEing) process (Horton et al., *BioTechniques* 8:528, 1990), or by other methods known in the art. The mutant expression vector is then expressed in cells, and the biological activity of the CD40L encoded by the mutant is determined using one or more of the assays for biological activity described herein as well as in U.S. Ser. No. 07/969,703, Armitage et al., *Nature* 357:80, 1992, Fanslow et al., *J. Immunol.* 149:655, 1992, and Spriggs et al., *J.Exp. Med.* 176:1543 (1992).

The observation that normal B cell function could be restored by the addition of exogenous, biologically active CD40L supports a therapeutic use of this molecule. Such therapy could comprise administering purified CD40L in a therapeutic composition comprising an effective amount of CD40L in a suitable diluent or carrier. For therapeutic use, purified CD40L or a biologically active analog thereof is administered to a patient, for treatment in a manner appropriate to the indication. CD40L pharmaceutical compositions (for example, in the form of a multimeric soluble extracellular domain, or a fragment thereof) can be given by bolus injection, continuous infusion, sustained release from implants, or other suitable technique.

Typically, a CD40L therapeutic agent will be administered in the form of a pharmaceutical composition comprising purified CD40L polypeptide in conjunction with physiologically acceptable carriers, excipients or diluents. Such carriers will be nontoxic to patients at the dosages and concentrations employed. Ordinarily, the preparation of such compositions entails combining a CD40L polypeptide with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

A gene encoding biologically active CD40L may also be introduced into T cells (preferably CD4+ T cells) obtained from an individual with abnormal or defective CD40L using gene transfer techniques. The cells are isolated, and transfected with the biologically active CD40L gene; they are subsequently re-administered to the individual, and will then correct the symptoms of the syndrome by producing biologically active CD40L.

Numerous methods have been developed for introducing exogenous genes into mammalian cells, such as by transfection or by infection. These transduction methods may be physical in nature, or they may rely on the use of recombinant retroviral vectors encoding DNA which can be transcribed to RNA, packaged into infectious viral particles and used to infect target cells and thereby deliver the desired genetic material.

Many different types of mammalian gene transfer and expression vectors have been developed (see, Miller and Calos, eds., "Gene Transfer Vectors for Mammalian Cells," *Current Comm. Mol. Biol.*, Cold Spring Harbor Laboratory, New York, 1987). Naked DNA can be physically introduced into mammalian cells by transfection using any one of a number of techniques including, but not limited to, calcium phosphate transfection (Berman et al., *Proc. Natl. Acad. Sci. USA* 84 81: 7176, 1984) DEAE-Dextran transfection, protoplast fusion (Deans et al., *Proc: Natl. Acad. Sci. USA* 84 81: 1292, 1984), electroporation (Potter et al., *Proc. Natl. Acad. Sci. USA* 84 81: 7161, 1984), lipofection (Felgner et al., *Proc. Natl. Acad. Sci. USA* 84:7413, 1987), polybrene transfection (Kawai and Nishzawa, *Mol. Cell. Biol* 4:1172, 1984) and direct gene transfer by laser micropuncture of cell membranes (Tao et al., *Proc. Natl. Acad. Sci. USA* 84 84:4180, 1987).

Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., *Proc. Natl. Acad. Sci. USA* 84 82:158, 1985), adenoviruses (Karlsson et al., *EMBO J.* 5:2377, 1986), adeno-associated virus (LaFace et al., *Virology* 162:483, 1988) and retroviruses (Coffin, 1985, p17–71 in Weiss et al (eds.), *RNA Tumor Viruses*, 2nd ed., Vol 2, Cold Spring Harbor Laboratory, New York).

Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., *Oncogene* 3:123, 1988), and infection with recombinant adenovirus (Karlsson et al., supra; Ruether et al., *Mol. Cell. Biol.* 6:123, 1986) adeno-associated virus (LaFace et al., supra) and retrovirus vectors (Overell et al., *Oncogene* 4:1425, 1989). Primary T lymphocytes have been successfully transduced by electroporation (Cann et al., supra, 1988) and by retroviral infection (Nishihara et al., *Cancer Res.* 48:4730, 1988; Kasid et al., supra, 1990).

Gene targeting technology utilizing embryonic stem cells has made it possible to create transgenic mice exhibiting defined changes in a selected gene (Waldman A. S. 1992, *Crit. Rev. Oncol. Hematol.* 12(1):49–64; Huang M. T. 1993, *Lab. Anim. Sci.* 43(2):156–159; Koller and Smithies, 1992, *Annu. Rev. Immunol.* 10:705–730; Joyner A. L. 1991, *Bioessays.* 13(12):649–656; Smithies O., 1993 *Trends Genet.* 9(4):112–116). For example, a probe is prepared from a cDNA of the desired gene, and used to identify the actual gene in a genomic library. The structure of the gene is determined, and the desired change(s) developed. Recombinant DNA technology is used to prepare a vector that will introduce the desired change(s) in the gene of an embryonic stem cell by homologous recombination.

The altered ES cells are then injected into blastocysts, in which they contribute to the formation of all tissue types, including germ cells. The animals that develop from such blastocysts are referred to as chimeric. When the chimeric animals are bred, germ cells that contain the mutation give rise to animals that lack the functional gene. Such animals are referred to as "knockout" (KO) animals. Many examples of KO mice are known; some of these animals exhibit a phenotype similar to that seen in certain human genetic diseases, and thus serve as useful animal models.

CD40-L KO mice are likely to be of great interest to scientists investigating the cognate interactions between T and B cells in thymus-dependent antibody responses, as well as various aspects of immunoglobulin isotype switching. The role of CD40-L in human X-linked hyper-IgM syndrome indicates that CD40-L KO mice would be a valuable asset for testing possible treatments (i.e. administration of soluble, recombinant ligand) for hyper IgM. Additionally, CD40-L knockout mice are of interest for many different types of investigation, in that these animals have an exquisitely defined genetic defect that is expected to disable one specific cellular interaction necessary for an immune response. Thus, CD40-L KO mice are expected to be useful as models for testing vaccine preparations or immune response modifiers, in defining the role of T cells and B cells in various diseases and syndromes (including infectious disease), and in developing treatments for hyper IgM syndrome and other conditions which result from, or are linked to, abnormality in the interaction of T and B cells.

The following examples are intended to illustrate particular embodiments and not limit the scope of the invention. The pertinent disclosure of all references is incorporated by reference herein.

EXAMPLE 1

Mapping of the CD40L Gene

Using a cDNA corresponding to the coding region of the murine CD40L gene (Armitage et al., *Nature* 357:80, 1992), the chromosomal location of the murine CD40 locus was determined by interspecific backcross analysis using progeny derived from mating of [(C57BL/6J×*Mus spretits*)F1 X C57BL/6J] mice. This interspecific backcross mapping panel has been typed for over 1100 loci that are well distributed among all the autosomes as well as the X chromosome (Copeland and Jenkins, *Trends Genet.* 7:113, 1991). C57BL/6J and *Mus spretus* DNAs were digested with several restriction endonucleases and analyzed by Southern blot hybridization for informative restriction fragment length polymorphisms (RFLPs) using a mouse CD40L cDNA probe. The mapping results indicate that the CD40L gene (CD40l) is located in the proximal region of the murine X chromosome, linked to hypoxanthine-guanine phosphoribosyl transferase (Hprt), bone morphogenic protein-2b2 (Bmp-2b2) and connexin-32 (Cnx-32). A description of the probes and RFLPs for the loci linked to Cd40l including Hprt, Bmp-2b2, and Cnx-32.have been reported previously (M. E. Dickinson et al., *Genomics* 6:505, 1990; J. A. Haefliger et al., *J. Biol. Chem.* 267:2057, 1992). Recombination distances were calculated as described (E. L. Green, in *Genetics and Probability in Animal Breeding Experiments*, Oxford University Press, New York, 1992, pp. 77–113) using the computer program SPRETUS MADNESS. Gene order was determined by minimizing the number of recombination events required to explain the allele distribution patterns. The determined recombination frequencies place the Cd40l gene 1.5+/−1.1 centiNorgans distal of the Hprt locus. HPRT maps to the q26 region of the human X chromosome, suggesting that the human homologue of the CD40L would also map to this region. This was confirmed by the situ hybridization studies of human metaphase chromosomes using a human CD40L cDNA probe. Human metaphase chromosomes were obtained from lymphocytes of two normal male donors. Hybridization was carried out using a human CD40L probe labeled with $^3$H to a specific activity of $1\times10^6$ cpm/µg as described (J. D. Marth et al., *Proc. Natl. Acad. Sci. USA* 83:7400, 1986). The final probe concentration was 0.4 ng/µg of hybridization mixture. The slides were exposed for 5–7 weeks. Chromosomes were identified by Q-banding. Of 115 sites of hybridization scored, 18 (16%) were located on the distal portion of the long arm of the X chromosome. The largest number of grains was at band q26, with no significant hybridization on other human chromosomes.

EXAMPLE 2

Analysis of CD40L Expression on Hyper-IgM Patient T Cells

Expression of CD40L was examined in four adolescent patients whose clinical and laboratory findings were consistent with primary X-linked hyper-IgM syndrome. Three of these patients represented sporadic cases with no similarly affected male relatives. The fourth patient belonged to a family with a documented three generation pedigree showing a classic X-linked inheritance of hyper IgM syndrome.

The expression of CD40L was examined directly on peripheral blood T cells purified from the four hyper-IgM patients. Resting peripheral blood T cells express undetectable levels of both CD40L mRNA and protein, however, stimulation with antibody specific for CD3 for 16 hours results in a significant increase in the level of mRNA and cell surface protein (Spriggs et al., J. Exp. Med. 176:1543, 1992). Therefore, peripheral blood leukocytes were purified from patient or control donor heparinized whole blood by separation over ficoll-hypaque. T cells were activated with immobilized CD3 mAb and analyzed by flow cytometry using a soluble form of CD40. This soluble CD40 protein (CD40.Fc), which was described in U.S. Ser. No. 07/969, 703 and in Fanslow et al., J. Immunol. 149:655, 1992, is a fusion protein containing the extracellular domain of human CD40 fused to the Fc region of human IgG1. All experiments included control cells from normal adult donors and in the case of Patients 1, 3, and 4, from age-matched unaffected males. Control cells for Patient 2 included an age-matched, race-matched male diagnosed with X-linked agammaglobulinemia (XLA), an unrelated immunodeficiency. In contrast to T cells from control donors, T cells from Patients 2, 3, and 4 failed to express any detectable CD40L upon activation by CD3 antibody. In some experiments, activated T cells from Patient 1 appeared to weakly bind CD40. However, activation of T cells from all 4 patients with immobilized CD3 mAb did result in expression of the alpha chain of the IL-2 receptor (L-2Rα), a common T-cell surface activation marker, at levels comparable to that seen on T cells from control donors. In addition, T cells from hyper-IgM patients showed normal proliferative responses to PHA or CD3 mAb plus IL-7. These data indicate that while hyper-IgM patients' T cells respond normally to mitogens or to activation through their T-cell receptors, they do not express wild type CD40L on their cell surfaces.

EXAMPLE 3

Nucleotide Sequence Analysis of CD40L From Hyper-IgM Patients

The nucleotide sequence of cDNA from the hyper-IgM patients of Example 2 was analyzed. Peripheral blood leukocytes (PBL) from patients or control donors were purified from heparinized whole blood on ficoll-hypaque. Cells were then stimulated by incubating overnight with immobilized CD3 antibody or PHA. RNA was extracted from the stimulated PBL using RNAzol (Biotecx, Houston, Tex.). Five to ten µg of total RNA was diluted in 10 µl water and heated at 68° C. for five minutes. To this mixture was added 1 µl RNasin, 2 µl 10X Perkin-Elmer PCR buffer, 1 µl 20 mM dNTPs, 2 µl random hexamer primer (Pharmacia, Uppsala, Sweden), and 100 U reverse transcriptase. The mixture was incubated at room temperature for 10 minutes, then 37° C. for 1 minute, and heat inactivated at 95° C. for 5 minutes. cDNA from this reaction was used as a template in PCR using the following reaction conditions: 5 µl of 10X Perkin-Elmer buffer,50 µM dNTPs, 1 µM primers, 2 µl of the cDNA reaction, and 1.25 U Taq polymerase (Perkin-Elmer) to a total volume of 50 µl. The mixture was denatured at 95° C. for 5 minutes, and after addition of Taq polyrnerase, 35 cycles of 55° C. for 1 minute, 72° C. for 1 minute, and 94° C. for 1 minute were performed. Two PCR reactions were performed to cover the entire cDNA. The primers used to amplify the 5' portion of the cDNA were 5'-CCAGAAGATACCATTTC-3' (SEQ ID NO:1) and 5'-AGCCCACTGTAACACAG-3' (SEQ ID NO:2). The primers for the 3' portion of the cDNA were 5'-CATGTCATAAGTGAGGC-3' (SEQ ID NO:3) and 5'-CATAAGGAGGATCCTAG-3' (SEQ ID NO:4). PCR fragments were filled in with Klenow (Pharmacia, Uppsala, Sweden), separated on 1.5% agarose gels, and the purified fragments were ligated into SmaI-cut pTZ19R for sequencing. Double stranded sequencing was performed manually with a Sequenase kit (USB, Cleveland, Ohio). Automated sequencing was performed on an Applied Biosystems Model 373A sequencer. In these experiments, control cells were provided by either unaffected age-matched controls, or in all cases, at least one normal adult donor. In addition, one adolescent male diagnosed with X-linked lymphoproliferative disorder (XLP), an unrelated immunodeficiency, was included as a control for Patient 1. Nucleotide sequence analysis of the resultant cDNAs indicated that single point mutations occurred in the CD40L of three of the four hyper-IgM patients. To ensure that these changes were not artifacts introduced during PCR amplification, all reactions, including the initial cDNA synthesis reaction, were performed at least in duplicate. Each nucleotide change is unique, and all occur in the extracellular domain of the CD40L. These changes result in the following amino acid changes: a glycine to valine change at position 227 in Patient 1; a leucine to proline change at position 155 in Patient 2; and a threonine to asparagine change at position 211 for Patient 3. The CD40L cDNA generated from Patient 4 did not appear to contain any nucleotide changes within the coding region. Because the biological analysis performed on this patient clearly indicates a lack of functional CD40L, another mechanism, possibly involving the 5' or 3' non-coding sequences, must be responsible for the absence of the CD40L on T cells in Patient 4. No nucleotide changes were found in the CD40L cDNAs from any control samples, which included the XLP patient.

EXAMPLE 4

Site-directed Mutagenesis of the CD40L cDNA

To test whether the nucleotide changes detected in Example 3 affected the expression of the CD40L or its ability to bind to CD40, the two nucleotide changes found in Patient 1 and Patient 2 of Example 2 were introduced separately into a mammalian expression vector containing the complete coding region for the human CD40L using site-directed mutagenesis. A cloning vector containing human CD40L sequence, designated hCD40-L, was deposited with the American Type Culture Collection, Rockville, Md. (ATCC) on Dec. 6, 1991, under accession number 68873. Mutants were constructed using the gene splicing by overlap extension (SOEing) process (Horton et al., BioTechniques 8:528, 1990). The primer used to recreate the mutation found in Patient 1 was 5'-TGCGGGCAACAATCC ATTCACTTGGGAGTATFFGAATMTGCAA (SEQ ID NO:5). The primer used to recreate the mutation found in Patient 2 was 5'-CCATGAGCAACAACTTGGTAACCC CGGAAAATGGGAAACAGC (SEQ ID NO:6). The remainder of the necessary primers were generated from the CD40L sequence (described in U.S. Ser. No. 07/969,703 and in Armitage et al., Nature 357:80, 1992 and Spriggs et al., J.Exp. Med. 176:1543, 1992). The resultant vectors were referred to as Mutant 1 and Mutant 2, respectively. The introduction of the appropriate nucleotide change was confirmed in the actual expression vectors by sequence analysis of the entire coding region. The human embryonic kidney cell line, 293, was transfected with vectors carrying either the wild type or the mutagenized CD40Ls, and on day 3 post transfection, cells were metabolically radiolabeled with $^{35}S$ Trans-label (ICN Radiochemicals, Irvine, Calif.). Cell lysates were prepared and examined for expression of CD40L protein by precipitation with a polyclonal serum directed against CV1/EBNA cells expressing the human CD40L, or with CD40.Fc. Cells transfected with the wild type CD40L expressed a 33 kD protein that can by readily precipitated using CD40.Fc. In contrast, cells transfected with either mutant form of CD40L did not express a protein recognized by CD40.Fc. Immunoprecipitation of identical lysates using the polyclonal antiserum, however, resulted in the recognition of a 33 kD protein from mutant as well as wild type transfected cells. This protein co-migrated with the CD40L protein recognized by the CD40.Fc and was not present in lysates transfected with vector alone. Consistent with these results, Northern blot analysis showed similar levels of CD40L-specific RNA in both wild type and mutant transfected cells.

Transfected cells were also examined by flow cytometric analysis. Cells transfected with either mutant form of CD40L were completely negative for CD40.Fc binding, while cells expressing the wild type CD40L showed strong CD40.Fc binding. To address the biological activity of the mutant CD40L proteins, cells transfected with wild type or mutagenized CD40Ls were examined for their ability to induce proliferation and IgE secretion from purified tonsil B cells co-cultured with IL-4. In contrast to cells transfected with wild type ligand (Table 1), cells expressing either form of mutagenized CD40L were unable to induce B cell proliferation or IgE secretion, confirming the absence of functional CD40L on their cell surface.

TABLE 1

Mutagenized CD40 ligands are not biologically active

| Number of Transfected Cells | | Vector alone | Wild type | Mutant 1 | Mutant 2 |
|---|---|---|---|---|---|
| $3 \times 10^4$ | cpm* | 425 ± 93 | 6463 ± 911 | 375 ± 122 | 407 ± 92 |
| | IgE† | <0.3 | 25 ± 2.8 | <0.3 | <0.3 |
| $1 \times 10^4$ | cpm* | 450 ± 38 | 4553 ± 405 | 496 ± 170 | 367 ± 64 |
| | IgE† | <0.3 | 5.7 ± 2.3 | <0.3 | <0.3 |
| $3 \times 10^3$ | cpm* | 414 ± 54 | 1710 ± 171 | 398 ± 143 | 501 ± 116 |
| | IgE† | <0.3 | 1.4 ± 0.4 | <0.3 | <0.3 |

*Tritiated thymidine incorporated by $1 \times 10^5$ purified tonsil B cells measured at day 4
†IgE secretion (ng/ml) by $1 \times 10^5$ tonsil B cells co-cultured for 10 days with 5 ng/ml IL-4

EXAMPLE 5

Hyper-IgM Patient B Cells Respond Normally to Wild Type CD40L

To address the ability of X-linked hyper-IgM B cells to respond to wild type CD40L, proliferation and isotype secretion assays were performed. T-depleted peripheral blood mononuclear cells (PBMC) (B-cell enriched populations) from all four patients from Example 2 showed a proliferative response to CD40L comparable to that seen with similarly purified PBMC from control donors. In contrast, no such proliferative response was seen in the T-cell depleted cultures of PBMC obtained from the XLA patient, consistent with the fact that the XLA disorder is characterized by the virtual absence of circulating, mature B lymphocytes.

Previous work has shown that culture of single donor PBMC in the presence of IL-4 results in the production of IgE (IgE secretion from $1 \times 10^5$ unfractionated to T-depleted PBMC was determined following 10 days culture with 5 ng/ml IL-4, together with 200 ng/ml G28-5 antibody (monoclonal antibody to CD40, obtained from Dr. E. A. Clark, University of Washington, Seattle, Wash.) or $1 \times 10^4$ fixed CV1/EBNA cells transfected with vector alone or human CD40L. Preparation of PBMC and determination of secreted IgE concentrations were performed as described in Fanslow et al., *J. Immunol.* 149:655, 1992. Results are expressed as the mean +/−SEM of triplicate cultures. PBMC from normal donors (Controls 1, 3, and 4) produced measurable amounts of IgE when cultured with IL-4 (Table 2). In contrast, no IgE production was detected from any of the four hyper-IgM patients cultured under the same conditions. Significantly, in 3 out of 4 cases (Patients 1, 2, and 4), the addition of recombinant CD40L or the CD40 ab, G28-5, to cultures containing hyper-IgM patients' PBMC restored their ability to secrete IgE. Similarly, the T-depleted PBMC (B-cell enriched cultures) from these three patients and from all controls examined secreted IgE in the presence of IL-4 plus either recombinant CD40L or G28-5 antibody (Table 2). In the case of Patient 3, no IgE was detected in PBMC cultured with IL-4 and recombinant CD40L or G25-8 antibody. The reason for these results is unclear. Additional PBMC were not available from this patient; thus, it was not possible to determine whether this lack of response was reproducible or due to experimental variation.

TABLE 2

PBMC from hyper-IgM patients can secrete IgE

| | | IgE Secreted* Patient/Control | | | |
|---|---|---|---|---|---|
| | | 1 | 2 | 3 | 4 |
| | | A. Unfractionated PBMC | | | |
| Vector alone | Patient | <0.3 | <0.3 | <0.3 | <0.3 |
| | Control | 8.6 ± 1.2 | <0.3 | 16.3 ± 2.9 | 22.9 ± 3.7 |
| CD40 ligand | Patient | 43.3 ± 4.8 | 51.0 ± 12.4 | <0.3 | 33.5 ± 6.0 |
| | Control | 73.4 ± 6.7 | <0.3 | 48.1 ± 4.4 | 25.7 ± 4.0 |
| G28-5 mAb | Patient | 76.4 ± 6.8 | 54.7 ± 12.5 | <0.3 | 55.0 ± 8.6 |
| | Control | 87.1 ± 9.8 | <0.3 | 87.2 ± 5.8 | 84.4 ± 8.2 |
| | | B. T-depleted PBMC | | | |
| Vector alone | Patient | <0.3 | <0.3 | <0.3 | <0.3 |
| | Control | <0.3 | <0.3 | <0.3 | <0.3 |
| CD40 ligand | Patient | 39.2 ± 4.4 | 22.6 ± 3.1 | <0.3 | 23.1 ± 6.3 |
| | Control | 128.4 ± 13.6 | <0.3 | 55.1 ± 4.6 | 80.2 ± 8.3 |
| G28-5 mAb | Patient | 69.4 ± 6.2 | 34.4 ± 11.9 | <0.3 | 45.5 ± 6.0 |
| | Control | 146.0 ± 12.2 | <0.3 | 93.5 ± 6.1 | 98.0 ± 9.5 |

*IgE secretion from $1 \times 10^5$ purified tonsil B cells was measured after 10 days co-culture with 5 ng/ml IL-4, together with 200 ng/ml G28-5 antibody or with CV-1/EBNA cells transfected with CD40L or vector alone.

EXAMPLE 6

Nucleotide Sequence Analysis of the CD40L Gene

The nucleotide sequence of the CD40L gene is determined using a genomic library prepared from human cells. Clones from the genomic library are digested with restriction enzymes to form restriction fragments which can be electrophoretically separated. The electrophoretically-separated restriction fragments are analyzed by Southern blot using oligonucleotide probes that are 30 to 40 oligonucleotides in length, prepared from various portions of the coding region of CD40L. Overlapping fragments are determined and sequenced; sequencing is performed on sufficient fragments to encompass the entire coding region of CD40L. PCR probes may be prepared based on the sequences of the regions flanking the intron-exon boundary for all exons. The PCR probes are used in a similar manner to that described in Example 3, to determine if there are abnormalities in the sequences of any nonoding regions present in CD40L genomic material. Such analysis will be useful, for example, in analyzing genomic material from cells obtained from a fetus through amniocentesis or chorionic villus sampling. The PCR probes derived in this manner will also be useful in analyzing genomic material, as may be necessary when there are no abnormalities detected in the coding region of a CD40L gene.

EXAMPLE 7

Generation of CD40L Knockout Mice

The type of DNA construct prepared is classified as a "replacement-type" vector in which a positively selectable marker (the neomycin resistance gene driven by the murine PGK-1 promoter) is flanked on both sides by regions homologous to the target gene (CD40-L). Such vectors are designed to replace a wild type allele with the altered version by homologous recombination through a double reciprocal crossover event involving the vector sequences homologous to the target. In contrast, random integration is thought to incorporate the entire molecule. Thus, to boost the efficiency of targeting, a negative selection marker (the HSV thymidine kinase, or TK, gene) was inserted in the vector, at the end one region of homology.

After a targeting vector was introduced into ES cells, a positive-negative selection (PNS) was initiated. The neomycin resistance gene confers resistance to G418, while the product of the HSV TK gene results in the transformation of gancyclovir into a toxic compound. Thus, in theory, only cells undergoing homologous recombination survived both selections. This scheme for vector construction and PNS has been well established (Mansour et. al. 1988, *Nature*. 336: 348–352).

Figure 1B:
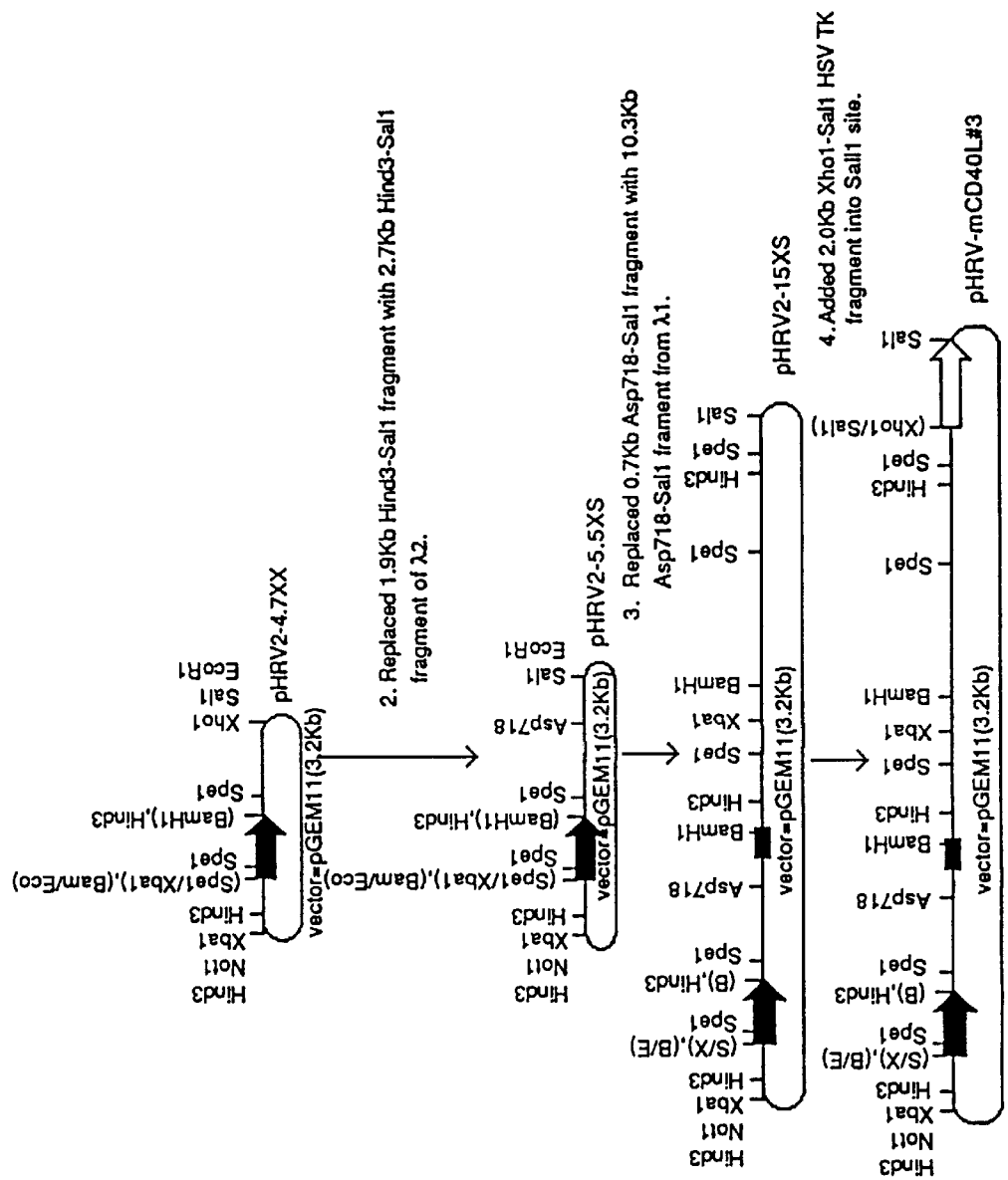

To facilitate construction of a gene targeting vector for the CD40L, a murine genomic DNA library constructed from the strain 129SV (Stratagene, Cat#946305) was screened with a radiolabeled murine CD40L cDNA probe containing the complete coding region (Armitage et. al. 1992, *Nature*. 357:80–82, and U.S. Ser. No. 07/969,703). Six clones were isolated and two, designated $\lambda_1$ and $\lambda_2$, were chosen for further analysis based on evidence that they overlapped and each contained a sizable portion of the gene. A restriction map and exon location and sizes were determined using standard methodology, and are shown in FIG. 1.

A 6.8 Kb BamH1-Spe1 fragment from $\lambda 2$ was subcloned into pGEM11 digested with BamH1+Xba1. The resulting plasmid, p$\lambda$2–6.8BS, was digested with BamH1 and the ends blunted by treatment with Klenow fragment. A blunted 1.5 Kb EcoR1-BamH1 fragment from pPGK/Neo(WT)A- was inserted, creating p6.8Neo. This construct was digested with Xho1, blunted with Klenow fragment, and a 20 Kb, blunted Hind3-Asp718 fragment from $\lambda 1$ was inserted. The resulting plasmid, p6.8NeoHA, was digested with Xho1 and a 20 Kb Xho1-Sal1 fragment from pTGX105-9 (containing the HSV TK gene) was inserted to create pHRV-mCD40L#1.

pHRV-mCD40L#1, upon homologous recombination, would result in a CD40L allele lacking only exon 4. Further analysis indicated that this mutation may not have completely abolished function of the CD40-L gene. Therefore, exon 3 was also deleted, in the following manner. p$\lambda$2–6.8BS was digested with Spe1+BamH1 and a resulting 7.7 Kb fragment was purified. This was ligated with a 5.5 Kb BamH1-Xba1 fragment of pHRV-mCD40L#1 to create pHRV-mCD40L#2. This vector, upon homologous recombination, should result in a mutant CD40L allele lacking both exons 3 and 4.

pHRV-mCD40L#2 was electroporated into embryonic stem cells at 200V and 960 $\mu$F. Cells were cultured on a feeder layer of gamma-irradiated, neomycin-resistant STO cells expressing Leukemia Inhibitory Factor (LIF). Cells were selected in 175 $\mu$g/mL G418+2 mM gancyclovir for approximately 10 days. Clones were then plated singly and analyzed via PCR in pools of 5 clones. PCR was performed with the CD40L specific primer TGX106.19 (5'-GGCAAGGTCAAGCTCATCC-3'; SEQ ID NO:9) in conjunction with the antisense neomycin resistance gene primer, TGX63.20 (5'-GATATTGCTGAAGAGCTTGG-3'; SEQ ID NO:10). A total of 800 doubly resistant clones (680 in the 129SV-derived ES line, AB1, and 120 in the C57BL/6-derived ES line, B22) were screened for homologous recombination events in this manner. No positive clones were identified.

After several unsuccessful attempts with pHRV-mCD40L#2, a third plasmid with a longer region of homology to the 3' end of the CD40-L gene was prepared. pHRV-mCD40L#2 was digested with Xba1 and Xho1, and a 4.7 Kb fragment was subcloned into pGEM11 to create pHRV2-4.7XX. A 1.9 Kb Hind3-Sal1 fragment was replaced with a 2.7 Kb Hind3-Sal1 fragment from $\lambda 2$. This plasmid was named pHRV2-5.5×S. A 0.7 Kb Asp718-Sal1 fragment was replaced with a 10.3 Kb Asp718-Sal1 fragment from $\lambda 1$ to create pHRV2-15×S. This plasmid was subsequently digested with Sal1 and a 20 Kb Xho1-Sal1 fragment from pTGX105-9 (containing the HSV TK gene) was inserted. This resulted in pHRV-mCD40L#3, which was deposited with the American Type Culture Collection (ATCC) under the conditions of the Budapest Treaty on Jan. 19, 1994, and given ATCC Accession number 69537. Homologous recombination with pHRV-mCD40L#3 results in the same mutation as pHRV-mCD40L#2, namely the removal of exons 3 and 4.

pHRV-mCD40L#3 was electroporated and ES cells selected as described previously. PCR screening was performed using the CD40L specific primer TGX124.19 (5'-GTATGTGGCTGAACACCTG-3'; SEQ ID NO:11) and the antisense PGK/Neo primer, TGX53.18 (5'-CTTGTGTAGCGCCAAGTG-3'; SEQ ID NO:12). A total of 1191 doubly resistant clones (760 in AB1, 231 in B22, and 200 in a 129SV-derived ES line, D3) were obtained. Several positives were identified and subjected to karyotypic analysis, and a clone in the D3 line, D3 CD40L3 #9-72, was found to have a normal karyotype.

Targeted mutation of the CD40L gene was verified by genomic Southern blot analysis. Genomic DNAs from D3 CD40L3 #9-72 and wild type D3 were digested with Pst1, electrophoresed in agarose, blotted to nitrocellulose, and probed with a radiolabeled 400 bp Xba1-Pst1 fragment which lies just upstream of the 5' terminus of pHRV-mCD40L#3. This probe hybridized with a 9.0 Kb Pst1 fragment in the wild type D3 genome. Gene targeting, however, introduced a new Pst1 site (in PGK/Neo) 2.2 Kb 3' of the 5' Pst1 site. Thus, only a 2.2 Kb Pst1 fragment hybridized with the probe in the D3 CD40L3 #9-72genome.

D3 CD40L3 #9-72 cells were injected into day 3.5 blastocysts isolated from C57BL/6 mice, which have a black coat color. Injected blastocysts were carried to term in pseudopregnant Swiss Webster female mice. D3 CD40L3 #9-72 was created in ES cells derived from the 129SV strain which has a black agouti (brown) coat color. Chimeric offspring were identified by the presence of a mixed coat color (black and brown). Male chimeras were mated with wild type C57BL/6 females. Germline transmission of the mutant CD40-L allele was identified by the presence of black agouti female offspring. These females are heterozygous at the CD40-L locus.

Heterozygous females were mated to wild type male C57BL/6 mice. According to standard Mendelian genetics, 50% of all male offspring are expected to be hemizygous for the CD40-L mutation and thus would be expected to display a hyper-IgM phenotype. Hemizygous males are mated to heterozygous females to perpetuate the strain. Additionally, a congenic 129SV strain exhibiting the mutant CD40-L allele may be developed, for example, by backcrossing heterozygous females to wild type 129SV males. Alternatively, male chimeras that transmit the mutant CD40-L gene efficiently are mated to 129SV females. Germline transmission of the mutant X-chromosome would result in heterozygous 129SV females, which are mated to wild type 129SV male to obtain hemizygous 129SV males exhibiting the mutant CD40-L. The hemizygous male 129SV mice are mated to heterozygous 129SV females to produce homozygous females.

Figure 3:
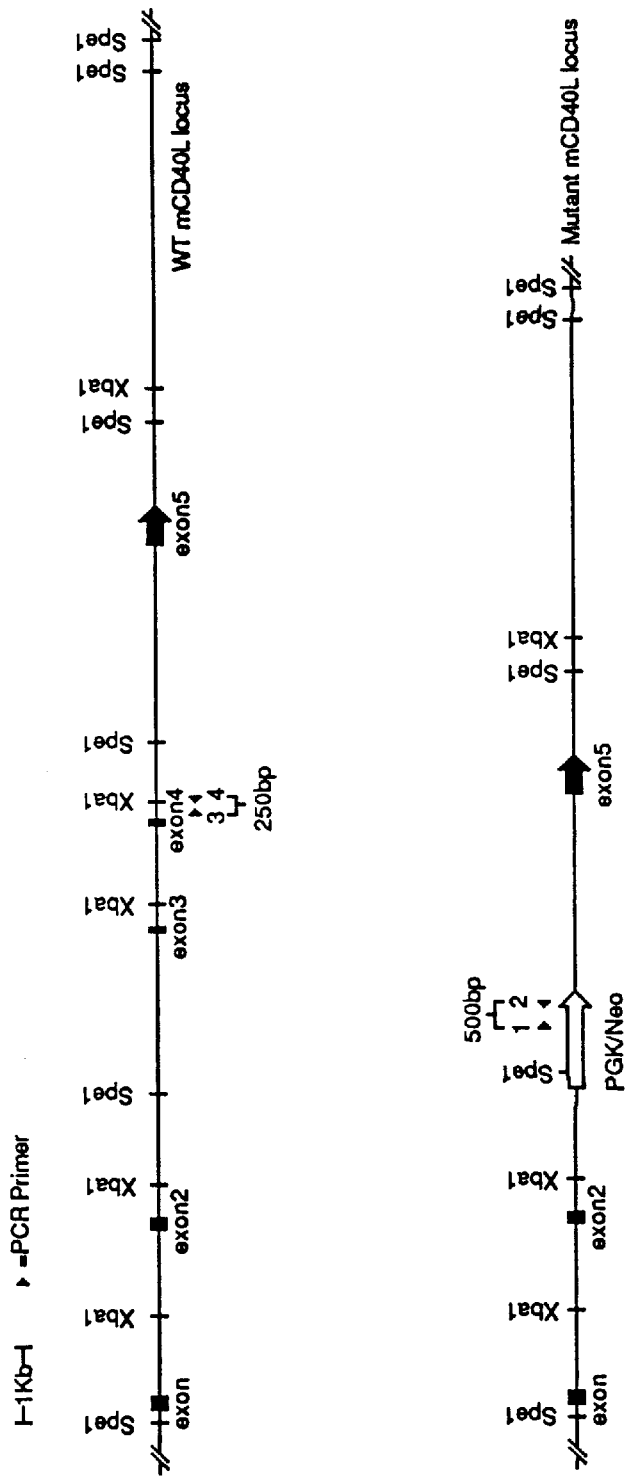
FIG. 3 presents a PCR scheme for genotype determination. PCR primer 3 corresponds to SEQ ID NO:13; PCR primer 4 corresponds to SEQ ID NO:14; PCR primer 1 corresponds to SEQ ID NO:15, and PCR primer 2 corresponds to SEQ ID NO:16.

The allelic state (i.e. wild type vs. heterozygous vs. homozygous mutant (hemizygous mutant in males)) is determined with a simple PCR scheme described in FIG. 3. DNA from a tissue sample (blood or ear biopsy sample) is subjected to PCR amplification using four primers. TGX157.23 (5'-CCCAAGTGTATGAGCATGTGTGT-3'; SEQ ID NO:13) and TGX156.23 (5'-GTTCCTCCACCTAGTCATTCATC-3'; SEQ ID NO:14) are specific to a region on the CD40-L gene just 3' of exon 4, and amplify a 250 bp fragment. This region has been deleted in the mutant allele. Neo1 (5'-GCCCTGAATGAACTGCAGGACG-3'; SEQ ID NO:15) and Neo2 (5'-CACGGGTAGCCAACGCTATGTC-3'; SEQ ID NO:16) are specific for the 3' end of the neomycin resistance gene. These primers amplify a 500 bp fragment specific to the mutant allele. The presence of the mutant allele is determined by Southern blot analysis substantially as described above.

Figure 2:
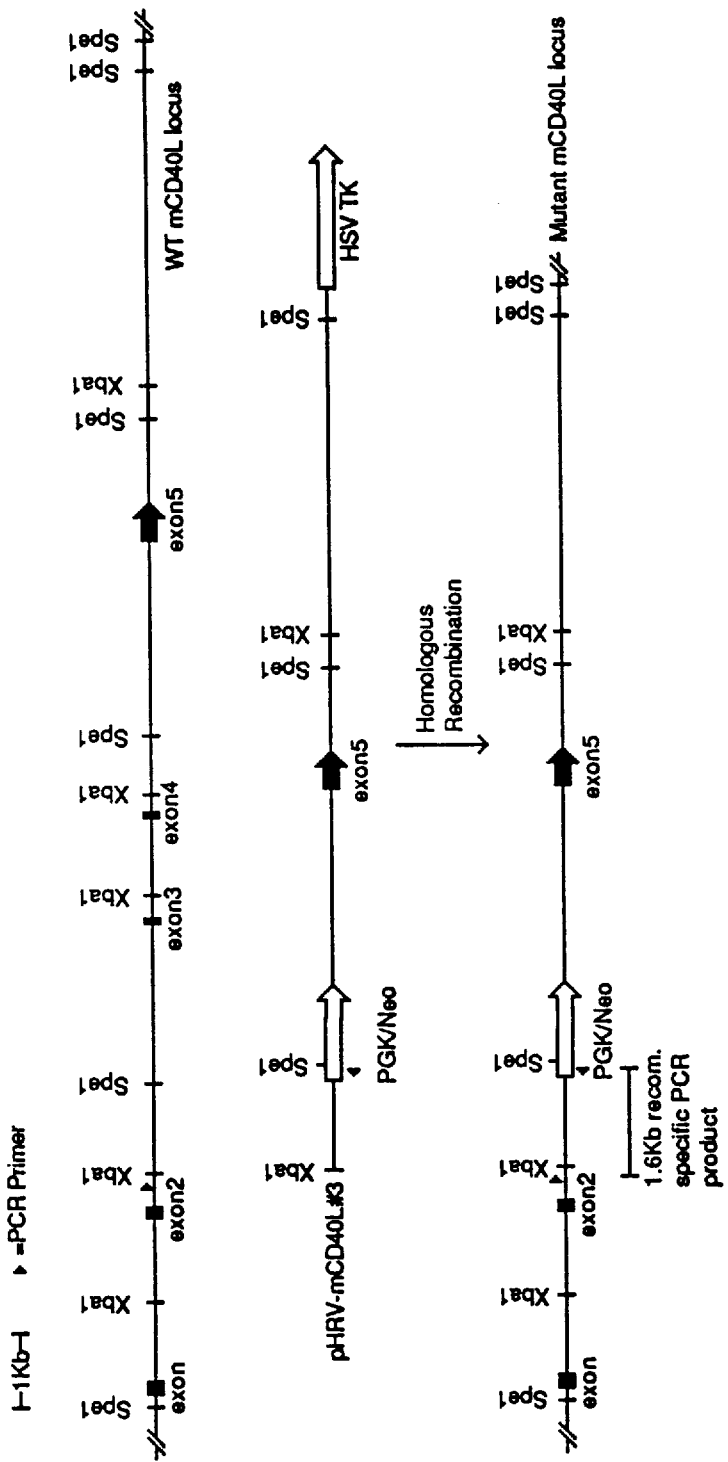
FIG. 2 illustrates the gene targeting scheme for pHRV-mCD40L#3.

A heterozygous female was obtained, and her allelic state analyzed according to the PCR scheme described above and outlined in FIG. 2. She was mated to a wild type C57BL/6 male as previously described. A sample from one potentially hemizygous male offspring thereof was analyzed as described above and outlined in FIG. 3; results of the analysis indicated that exons 3 and 4 were absent from the CD40-L gene, indicating that the mouse was hemizygous.

What is claimed is:

1. A population of CD4$^+$ T cells obtained by a process comprising the steps:
   (a) isolating CD4$^+$ T cells from an individual afflicted with hyper IgM syndrome; and
   (b) introducing into the cells a vector comprising a nucleic acid that encodes a polypeptide comprising SEQ ID NO:8.

\* \* \* \* \*